United States Patent [19]
Schulman et al.

[11] Patent Number: 5,651,767
[45] Date of Patent: Jul. 29, 1997

[54] REPLACEABLE CATHETER SYSTEM FOR PHYSIOLOGICAL SENSORS, STIMULATING ELECTRODES AND/OR IMPLANTABLE FLUID DELIVERY SYSTEMS

[75] Inventors: Joseph H. Schulman, Santa Clarita; Alfred E. Mann, Beverly Hills; Charles L. Byers, Canyon Country; Jack W. Love, Santa Barbara, all of Calif.

[73] Assignee: Alfred E. Mann Foundation for Scientific Research, Sylmar, Calif.

[21] Appl. No.: 587,881

[22] Filed: Jan. 11, 1996

Related U.S. Application Data

[63] Continuation-in-part of Ser. No. 239,357, May 6, 1994, Pat. No. 5,484,404.

[51] Int. Cl.⁶ ............................................. A61M 5/00
[52] U.S. Cl. ............................ 604/8; 128/635; 607/116; 623/12
[58] Field of Search .......................... 623/1, 12; 600/17; 606/129, 191; 128/899, 635; 602/120; 604/8, 9

[56] References Cited

U.S. PATENT DOCUMENTS

| | | | |
|---|---|---|---|
| 4,373,527 | 2/1983 | Fischell | 128/260 |
| 4,484,987 | 11/1984 | Gough | 204/1 T |
| 4,494,950 | 1/1985 | Fischell | 604/66 |
| 4,496,349 | 1/1985 | Cosgntino | 128/899 |
| 4,627,906 | 12/1986 | Gough | 204/415 |
| 4,650,547 | 3/1987 | Gough | 204/1 T |
| 4,671,288 | 6/1987 | Gough | 128/635 |
| 4,692,147 | 9/1987 | Duggan | 604/93 |
| 4,703,756 | 11/1987 | Gough et al. | 123/635 |
| 4,781,798 | 11/1988 | Gough | 204/1 T |
| 4,809,704 | 3/1989 | Sogawa et al. | 128/635 |
| 4,890,620 | 1/1990 | Gough | 128/635 |
| 4,934,369 | 6/1990 | Maxwell | 128/637 |
| 4,944,299 | 7/1990 | Silvian | 128/419 |
| 4,954,129 | 9/1990 | Giuliani et al. | 604/53 |
| 5,001,054 | 3/1991 | Wagner | 435/14 |
| 5,156,620 | 10/1992 | Pigott | 623/1 |
| 5,165,407 | 11/1992 | Wilson et al. | 128/635 |
| 5,190,041 | 3/1993 | Palti | 128/635 |
| 5,330,528 | 7/1994 | Lazim | 623/12 |

*Primary Examiner*—William E. Kamm
*Attorney, Agent, or Firm*—Fitch, Even, Tabin & Flannery

[57] ABSTRACT

A replaceable catheter system provides a way to replace an implantable sensor, electrode system, and/or fluid delivery/receiving system. The replaceable catheter system includes an implantable shunt, such as an arteriovenous shunt, attached to an implantable introducer. The introducer and implantable shunt are adapted for surgical implantation within a patient such that it extends from immediately below the patient's skin to the implantable shunt site. The replaceable catheter system further includes a replaceable catheter that is adapted to be contained within the introducer and properly aligned such that an implantable sensor, electrode system, and/or fluid delivery system that is carried by the replaceable catheter is placed in operative association with the implantable shunt and exposed to any fluids passing through the implantable shunt.

15 Claims, 7 Drawing Sheets

REPLACEABLE CATHETER SYSTEM FOR PHYSIOLOGICAL SENSORS, STIMULATING ELECTRODES AND/OR IMPLANTABLE FLUID DELIVERY SYSTEMS

This application is a continuation in part of U.S. patent application Ser. No. 08/239,357, filed May 6, 1994, to be issued as U.S. Pat. No. 5,484,404.

BACKGROUND OF THE INVENTION

The present invention relates to placing physiological and chemical sensors, stimulating electrodes, and/or implantable fluid delivery/receiving systems within living tissue relative to the vascular or neurological anatomy of an animal or human patient to perform a measurement, sensing or stimulation function. More particularly, the invention relates to a replaceable catheter system for such sensors, electrodes and fluid delivery/receiving systems.

Catheter systems are utilized for numerous measurement, sensing, and stimulation functions of body fluids and tissues, typically through an invasive procedure in which the catheter is inserted within a vascular member, e.g., a vein or artery, through which the investigated fluid flows or the catheter is implanted within the investigated tissue.

U.S. Pat. Nos. 4,484,987; 4,650,547; 4,781,798; 4,627,906; 4,671,288; 4,703,756; 4,890,620; 5,190,041; 5,165,407; and 5,001,054 describe various forms of glucose sensing electrodes and systems for detecting variations in and levels of glucose in blood. These patents are incorporated herein by reference.

U.S. Pat. No. 4,373,527 issued to Fischell describes an implantable programmable medication infusion system for injecting controlled quantities of a medication such as insulin to correct for fluctuations and stabilize the level of glucose within a human in response to control information stored within the implantable system.

US. Pat. No. 4,494,950 also issued to Fischell, describes a medication delivery system including a plurality of modules implantable within and/or wearable by a patient. In particular, an implanted glucose sensor generates and transmits information to one or more implanted modules or modules wearable by a patient. One of the implanted modules may comprise a medication infusion system responsive to the signals from the glucose sensor module for regulating the delivery of insulin to the patient. This patent also describes a system wherein a glucose sensor is connected to the end of a needle inserted through the skin of the patient and connected by an electrical lead to an external signal processing module for telemetering data to an implanted module including a medication release system for dispensing controlled amounts of medication into the patient in response to the signals from the sensor. Being attached to the tip end of the needle, the glucose sensor may be readily replaced as needed. U.S. Pat. No. 4,494,950 is incorporated herein by reference.

The related art, such as the Fischell '950 patent, describe systems in which readily replaceable sensors are located just under a patient's skin and on a needle tip or a similar removable device. Surgically implanted in vivo sensors and/or electrodes, on the other hand, still require surgical removal with the associated expense and risks of infection to the patient. Accordingly, there is a continuing need for a system that allows for the implanting of physiological sensors, and/or electrodes deep within the body of a human in areas where it is desired to sense a predetermined physiological activity, to receive a body fluid for analysis, or to stimulate tissue; and wherein the sensor, tube, and/or an electrode may be readily replaced without engaging in an extensive, expensive and risky surgical procedure. Also, for situations where the sensor, tube, or electrode may need to be replaced frequently, e.g. every six months, while the remainder of the system with which the sensor, tube or electrode is used may last for some time, e.g. several years, it is desirable that the system accommodate replacement of only the sensor, tube or electrode portion while leaving the balance of the support system intact.

Further, there is a similar need for replaceability in implantable fluid dispensing or receiving systems in the event the fluid delivery or receiving tubes become clogged and require replacement. In such situations, it is desirable to provide a system which allows for the non-surgical replacement of the fluid delivery or receiving tubes from the implantable fluid dispenser, such as a drug pump.

An additional concern relates to complications that may arise from the presence of a catheter system within a patient. While most catheters are constructed of a biocompatible material, protective mechanisms of the body generally operate on the invasive device to protect the body from the invasion of the foreign object. The most common protective mechanism of the body is encapsulation of the foreign object by a growth of isolating tissue. Obviously, the encapsulation of the end of a catheter from which the sensor or electrode protrudes will significantly reduce or cease the desired operation of the in vivo device. Further, and in particular with regard to a catheter placed within a blood vessel, blood clotting may occur at the end of the catheter where a sensor extends or is exposed, resulting in reduced effectiveness of the in vivo device, as well as blockage of the vessel by the clot. This is clearly an undesirable result.

Antithrombogenic chemical substances are known which reduce and slow the formation of thrombus, tissue growth, blood clotting and the encapsulation mechanism. For example, the substance known as "heparin" is a known anticoagulant which inhibits the action of the enzyme thrombin in the final stage of coagulation. The use of such substances with catheters and probes to reduce the undesirable effects of the body's protective mechanisms is well known in the art. For example, U.S. Pat. No. 4,954,129, issued to Giuliani, et al., teaches the use of these chemical substances for hydraulic flushing of thrombus or clotting material from within the lumen of an intravascular catheter having an open end from which a sensor probe extends. The Giuliani et al. patent further provides a defined process for flushing the bore of the catheter which utilizes a periodically increased velocity pulse of a flushant to remove incipient clot material formations. A specific structure is described and claimed in the Giuliani patent for centering a sensor probe within the lumen of the catheter and away from the catheter wall. Such structure provides fluid channels for the flow of the flushant through and from the end of the catheter around the probe sensor.

Another U.S. Pat. No. 4,934,369, issued to Maxwell, deals with the subject problems in a similar manner. While Maxwell teaches the technique of flowing Antithrombogenic fluid through and out of the end of the intravascular catheter around the sensors for measuring blood constituents, Maxwell also teaches the positioning of the sensors within the catheter lumen a select distance from the opening at the end of the catheter. Blood is permitted to enter the end of the catheter and/or through ports about the circumference of the catheter and mix with the Antithrombogenic fluid to forming an interface zone therebetween. The blood-fluid interface zone is washed back and forth over the sensors to expose the sensors to both blood and Antithrombogenic fluid by one of various described means for pulsing the flow of fluid within the catheter lumen.

While these references appear to disclose functional systems for applying an Antithrombogenic fluid to the environment of a sensor, both concern catheters which have an opening at their distal end which permit the sensor exposure to blood, either by the sensor extending through the opening to come into contact with blood, or by blood entering the end opening to contact the sensor immediately adjacent therewith. In both constructions the Antithrombogenic fluid flows through the lumen of the catheter and exits the end of the catheter, requiring some means to position the sensor centrally within the end opening in order for it to obtain uniform exposure and for uniform fluid infusion. However, many applications require sensors that are positioned other than centrally within the lumen of a catheter. Thus, it is apparent that improvements are needed in the techniques and methods for reducing the undesirable effects of the body's protective mechanisms on surgically implanted devices and catheters.

SUMMARY OF INVENTION

The present invention satisfies the needs for readily replaceable physiological or chemical sensors, fluid delivery or receiving tubes, and stimulating electrodes, implantable within a patient by connecting or combining a replaceable catheter to a surgically implantable shunt where the replaceable sensors, tubes, or electrodes are placed.

In accordance with one aspect of the invention, a replaceable catheter system is provided that includes a surgically implantable shunt, such as an arteriovenous shunt, formed of biocompatible material, to which an introducer is attached or connected. The introducer is disposed either within the internal flow passage of the implantable shunt or placed in a juxtaposition relation to the implantable shunt and on the exterior surface thereof. The replaceable catheter system further includes a replaceable catheter that is adapted to be placed within the introducer. Attached to the distal end of the replaceable catheter is one or more sensors, fluid delivery tubes or electrodes which are adapted to be placed in operative association with any bodily fluid flowing through the implantable shunt.

In use, a replaceable catheter is initially placed in an introducer that extends from the patient's skin to the implantation site proximate the implantable shunt. One or more sensors, electrodes, or fluid delivery or receiving tubes, are connected to the replaceable catheter. Importantly, such sensors, electrodes or tubes are adapted to be placed in operative association with the bodily fluid that flows through the implantable shunt. The replaceable catheter is sealably inserted through the introducer which directs the replaceable catheter either into or near the implantable shunt. Likewise, the replaceable catheter may be manually withdrawn from the introducer when it is desired to replace the sensors, electrodes and/or distal end of the fluid delivery or receiving tubes. Replacement catheters containing replacement sensors, electrodes, or fluid receiving or delivery tubes are then manually inserted through the patient's skin, into the introducer and directed to the appropriate position.

The present invention also addresses the need for reducing the undesirable effects of the body's protective mechanisms on implantable devices such as sensors, electrodes, and fluid delivery systems. This is accomplished through the use of protective sheaths for the sensors and internal storage and regulated delivery of anticoagulants, anti-bacteria substances, and tissue growth inhibitors proximate the implantation site.

Thus, it is an object of the invention to provide implantable sensors, electrodes, or delivery/receiving tubes that are positioned within or proximate an implantable shunt through which body fluids flow, and wherein the implantable shunt can be readily replaced when necessary.

BRIEF DESCRIPTION OF DRAWINGS

The objects, features, and advantages of the invention will be more apparent from the following more particular description thereof presented in conjunction with the following drawings, wherein.

DETAILED DESCRIPTION OF INVENTION

The following description of the invention includes the best mode presently contemplated for carrying out the invention. This description is not to be taken in a limiting sense, but is made merely for the purpose of describing the general principles of the invention. The scope of the invention should be determined with reference to the claims.

As is evident from the description that follows, an important aspect of the replaceable catheter system of the invention is the use of an implantable shunt, such as an arteriovenous shunt. An implantable shunt is typically a mechanical or fistulation device implanted to bypass or create an auxiliary flow of fluids from a particular origin to a particular destination. The arteriovenous shunt is one that connects the arterial and venous cannulas in a patient's arm or leg without going through the capillary system. An advantage of combining replaceable catheters with implantable shunts is that it allows the replaceable catheters to be easily placed in the body with reduced risk of infections and other medical complications. An arteriovenous shunt is preferred because it allows the replaceable catheter to be easily placed in the bloodstream. Further, since the blood flow through an arteriovenous shunt is significant, there is less likelihood of blood clots forming. More importantly, the implantation of arteriovenous shunts is a common and relatively simple surgical procedure. To that end, the implantation of an arteriovenous shunt coupled with an introducer and replaceable catheter is likewise a relatively simple surgical procedure.

FIGS. 1 through 4 illustrate various embodiments or arrangements of a replaceable catheter system made in accordance with the invention. Each of the embodiments illustrated include a replaceable catheter 30 having one or more sensing elements associated therewith, an introducer 20, and an implantable shunt 12. Replaceable catheter systems are further described in applicant's related patent application, Ser. No. 08/239,357, filed May 6, 1994, now U.S. Pat. No. 5,484,404 incorporated herein by reference.

As seen clearly in FIGS. 1 through 4, an introducer 20 is preferably a generally tubular member having a proximal end 22, a distal end 24, and an interior conduit 25 into which a replaceable catheter 30 may be inserted. The distal end 24 of the introducer 20 or catheter holder is adapted to be attached either internally or externally to an implantable shunt 12. The proximal end 22 includes an enlarged open neck 23 suitable for lying immediately under a patient's skin 29. The open end of the neck 23 is bounded by an outer annular flange 27 which functions as an annular attachment means for a self-sealing barrier 28, such as a sheet of manually pierceable rubber-like material or membrane. The introducer 20 is preferably of sufficient length so that it extends from an interior flow passage 14 of the implantable shunt 12 to the patient's skin 29 when surgically implanted.

Figure 1:
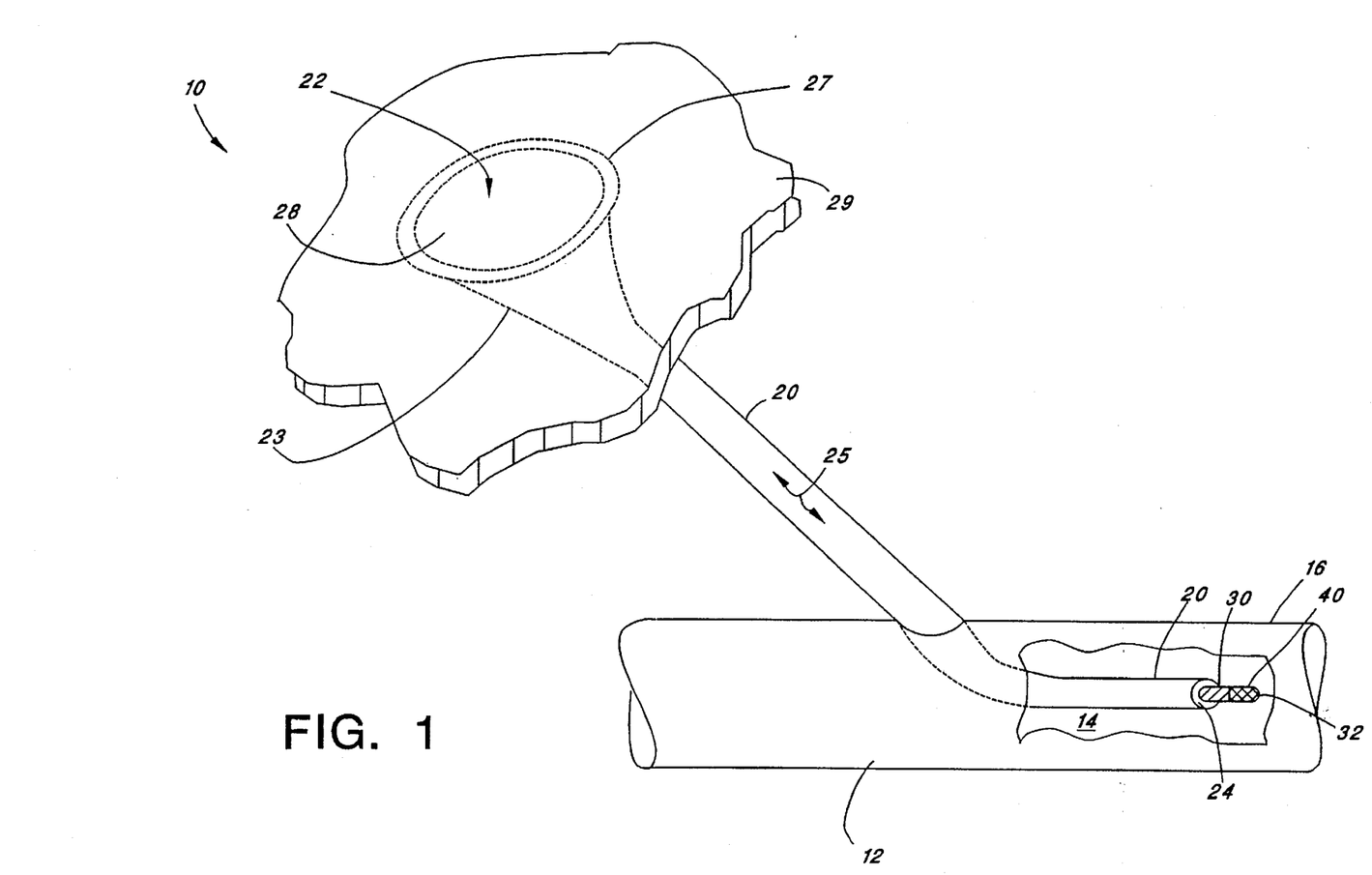
FIG. 1 is a diagrammatic representation of an interior sensor arrangement of the replaceable catheter system in accordance with the present invention.

As depicted in FIG. 1, sensors 40, electrodes 40', and/or fluid delivery or receiving tubes are carried by and connected to the replaceable catheter 30. (It is noted that while a sensor 40 is shown in FIG. 1, and the other figures, it is understood that electrodes 40' may be used in place of, or in combination with, the sensor 40. It is further noted that the sensors 40, electrodes 40', or tubes carried by the catheter 30 may be referred to herein as a "sensor/electrode".) The replaceable catheter 30 is inserted through the self-sealing barrier 28 of the introducer 20, through the interior conduit 25 of the introducer 20 and subsequently into the interior flow passage 14 of the implantable shunt 12, thus forming an interior configuration of the replaceable catheter system 10. Much like the introducer 20, the replaceable catheter 30 is of sufficient length such that it extends from just past the distal end 24 of the introducer 20 in the interior flow passage 14 of the implantable shunt 12 to a position immediately below the patient's skin 29. The replaceable catheter 30 is also adapted to be manually withdrawn from the interior flow passage 14 of the implantable shunt 12, through the interior conduit 25 of the introducer 20 and back through the self-sealing barrier 28 of the introducer 20 when it is desired to replace the sensors 40, electrodes 40' or tubes. Replacement catheters 30, containing replacement sensors 40, electrodes 40', or fluid receiving or delivery tubes are then manually inserted through the patient's skin 29, and directed into the interior flow passage 14 of the implantable shunt 12 via the introducer 20. In this first embodiment of the replaceable catheter system 10, the distal end 32 of the replaceable catheter 30 extends longitudinally within the implantable shunt 12 and beyond the distal end 24 of the introducer 20 in such a manner as to expose one or more physiological or chemical sensors 40, electrodes 40', or a fluid delivery or receiving tubes within the interior flow passage 14 of the implantable shunt 12. In this manner, the sensors 40, electrodes 40', and/or fluid delivery or receiving tubes are in direct communication with whatever body fluid, e.g., blood, passes through the implantable shunt 12.

Figure 2:
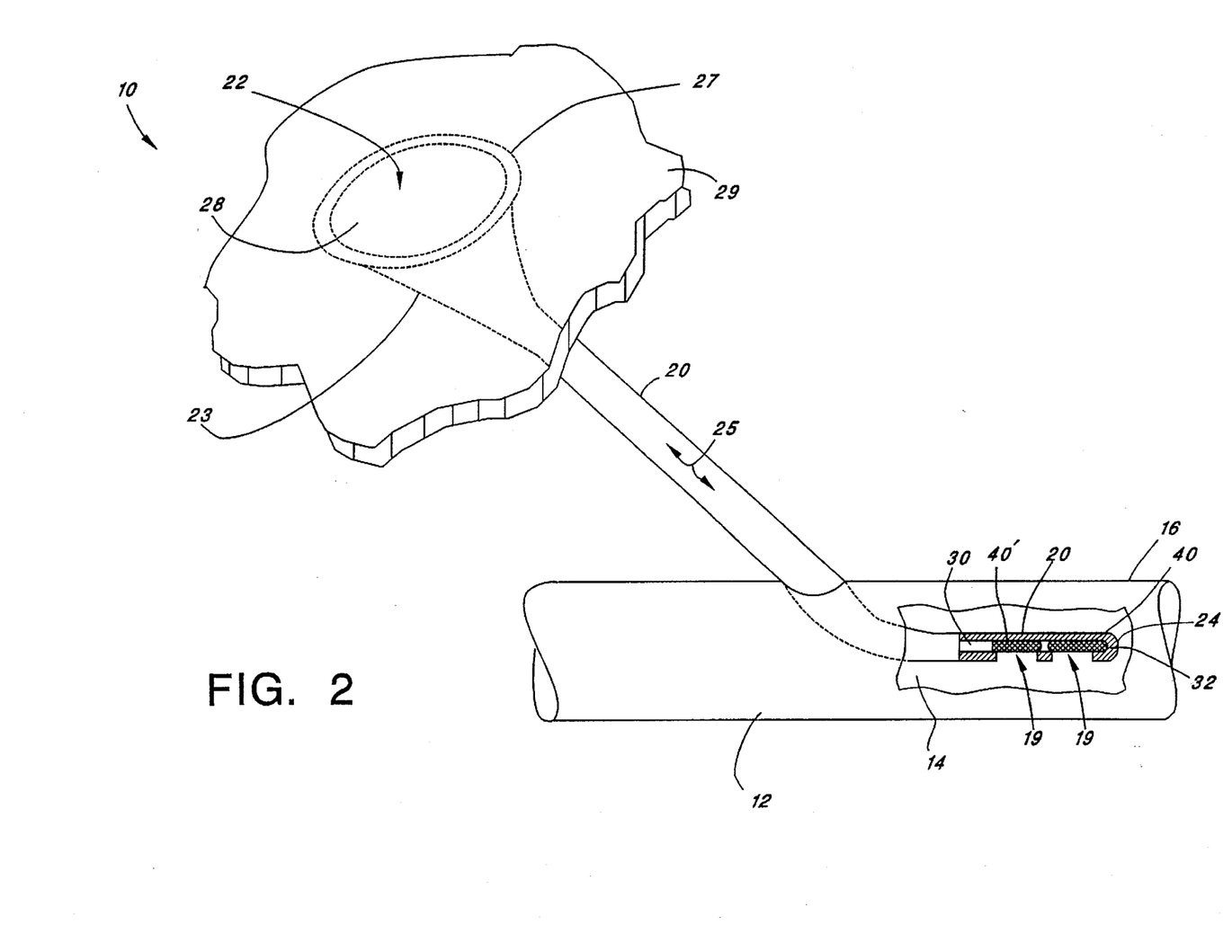
FIG. 2 is a diagrammatic representation of another embodiment of the replaceable catheter system illustrating a replaceable catheter, introducer, and implantable shunt in an alternate interior sensor arrangement.
Figure 3:
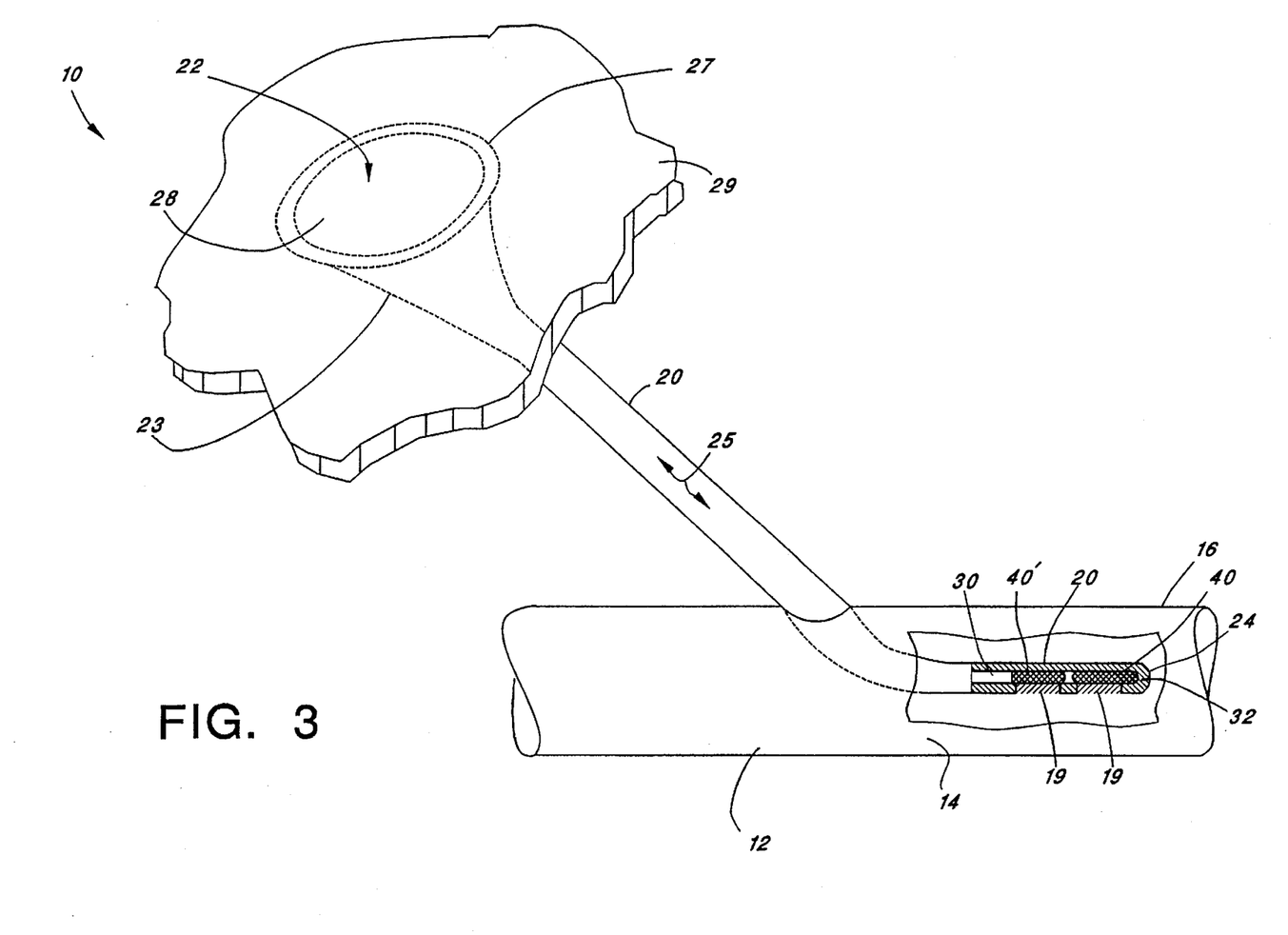
FIG. 3 is a diagrammatic representation of a yet another embodiment of the replaceable catheter system illustrating a replaceable catheter, introducer, and implantable shunt in an alternate interior sensor arrangement.

Alternatively, the sensors 40 or electrodes 40' in the interior configuration may be situated in non-direct communication with the bodily fluid passing through the implantable shunt 12, as shown in FIGS. 2 and 3. In this embodiment, the sensors 40 or electrodes 40' are completely contained within the introducer 20 or exposed only through windows 19 in the introducer. As seen more clearly in FIG. 2 and FIG. 3, the introducer 20 acts as a protective sheath which allows limited exposure to the sensors 40 or electrodes 40' through the windows 19 (FIG. 2) or alternatively, completely shrouds the sensors 40 and electrodes 40' such that only selected substances can permeate the protective sheath while other substances and bodily fluids are blocked (FIG. 3). For example, when the sensors 40 or electrodes 40' are placed in an arteriovenous shunt through which the patient's blood flows, the sensors 40 or electrodes 40' are preferably sealed within an introducer 20 of silicon rubber which functions as a protective sheath. Some oxygen will permeate through the silicon rubber sheath to the sensors 40 or electrodes 40', but other blood components such as red blood cells, plasma, platelets etc. do not infiltrate the protective sheath and continue through the arteriovenous shunt.

Figure 4:
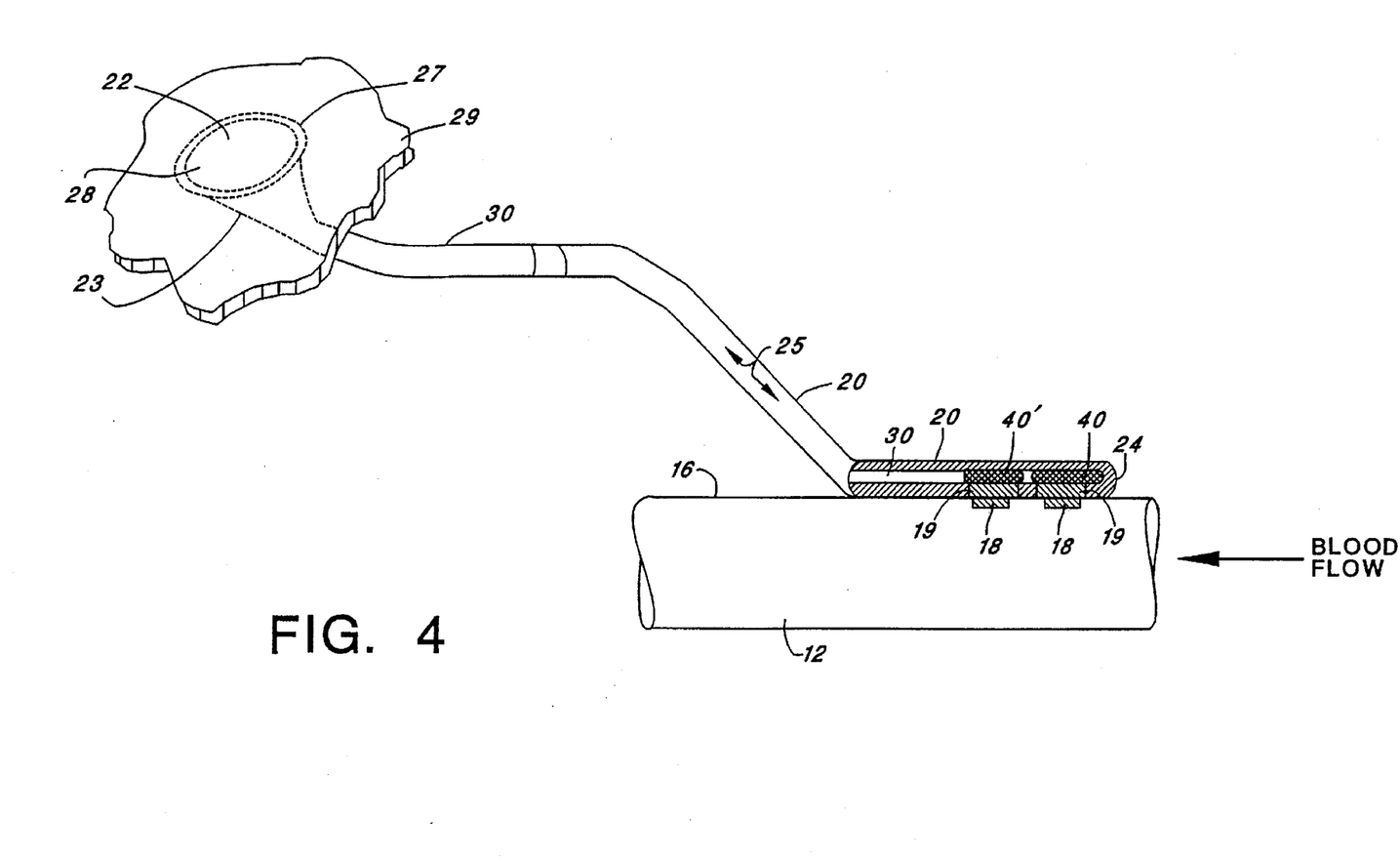
FIG. 4 is a diagrammatic representation of an external sensor arrangement of the replaceable catheter system in accordance with the present invention.

FIG. 4 illustrates yet another embodiment of the replaceable catheter system 10 wherein the introducer 20 containing the replaceable catheter 30 and sensors 40 and electrodes 40' is attached or otherwise disposed proximate to the exterior surface 16 of the implantable shunt 12. This arrangement exposes the sensors 40 or electrodes 40' to the appropriate bodily substance or chemical as the substances or chemicals permeate through strategically placed and aligned windows 18,19 in the implantable shunt 12 and introducer 20. In this exterior configuration of the replaceable catheter system 10, the introducer 20 is placed along the exterior surface 16 of the implantable shunt 12 and secured in a juxtaposition relationship with the implantable shunt 12 prior to surgically implanting the device. This embodiment of the replaceable catheter system 10 requires the distal end 32 of the replaceable catheter 30 to be aligned proximate to a window 18 in the implantable shunt 12 in such a manner as to expose the sensors 40 or electrodes 40' to the appropriate bodily substance or chemical as the bodily substance or chemical permeates through the window 18 of the implantable shunt 12 after implantation. As in the earlier described embodiments, the implanted replaceable catheter 30 is also manually withdrawn away from the exterior surface 16 of the implantable shunt 12 via the introducer 20 when it is desired to replace the sensors 40 or electrodes 40'. Replacement catheters 30 are then manually inserted through the patient's skin 29, into the introducer 20 which remains situated proximate the exterior surface 16 of the implantable shunt 12. The sensors 40 or electrodes 40' carried by the replaceable catheter are again aligned with the windows 19, 18 in the introducer 20 and implantable shunt 12 to assure adequate exposure to the chemical substances to be measured and thus allow proper operation of the sensors 40 and electrodes 40'.

In any of the aforementioned embodiments the sensors and electrodes are connected to an electronic package that includes circuitry for receiving and transmitting signals to or from the sensors and electrodes. The control device or module for the electronics package can be disposed either internally or externally to the patient. Similarly, any fluid delivery or receiving tubes are connected, as required, to suitable means for dispensing or receiving a fluid through such tubes. As with the control device or module, the fluid dispensing means can be disposed either internally or externally to the patient. Detailed disclosures of the control modules, fluid dispensing means and electronic packages as may be used herein are set forth in U.S. patent application Ser. No. 08/239,357, filed May 6, 1994, now U.S. Pat. No. 5,484,404 previously incorporated herein by reference.

Figure 5:
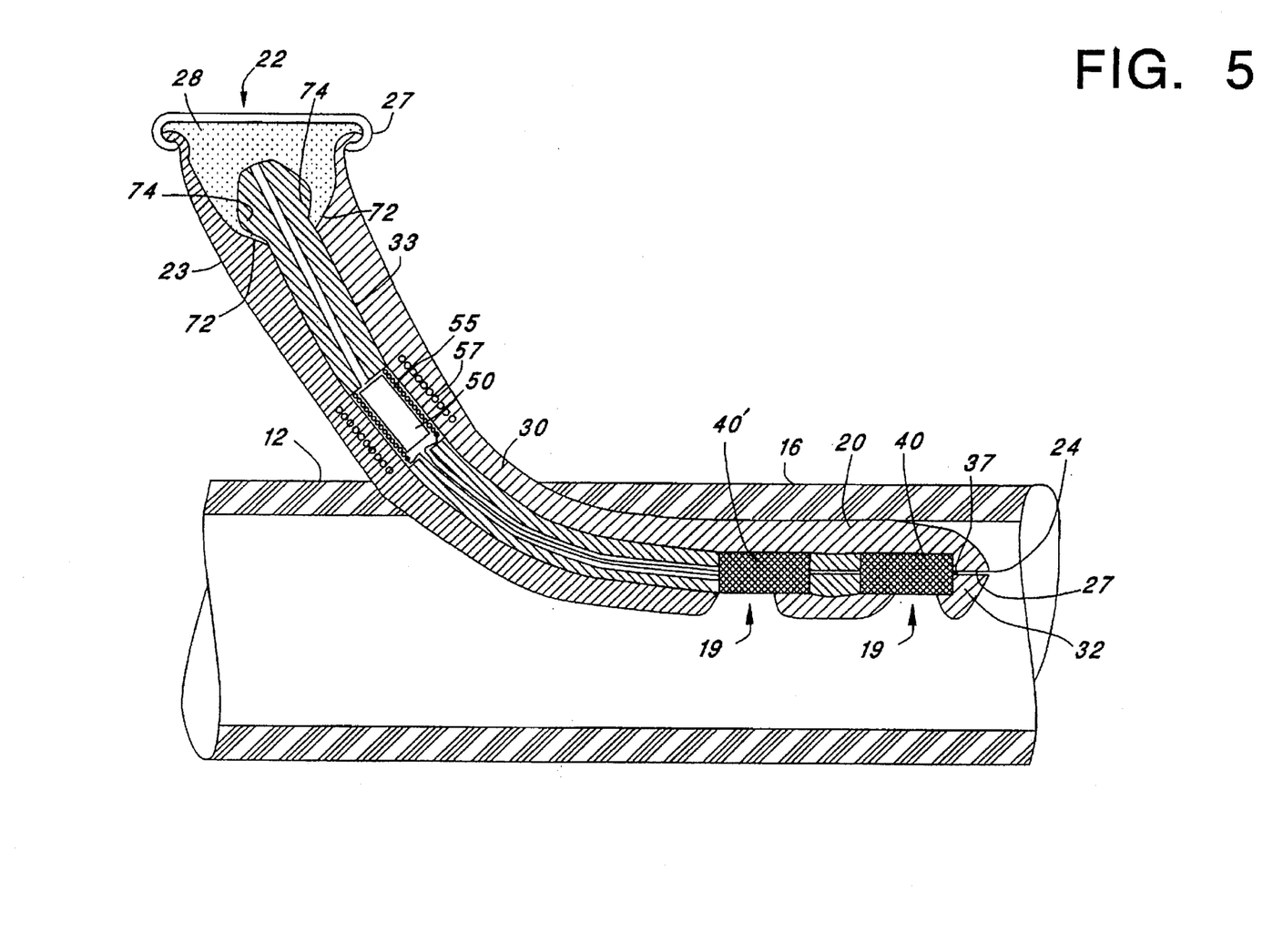
FIG. 5 is a cross sectional fragmentary view of the interior sensor arrangement of FIG. 3, illustrating the internal structure of the introducer, implantable shunt, and replaceable catheter.
Figure 6:
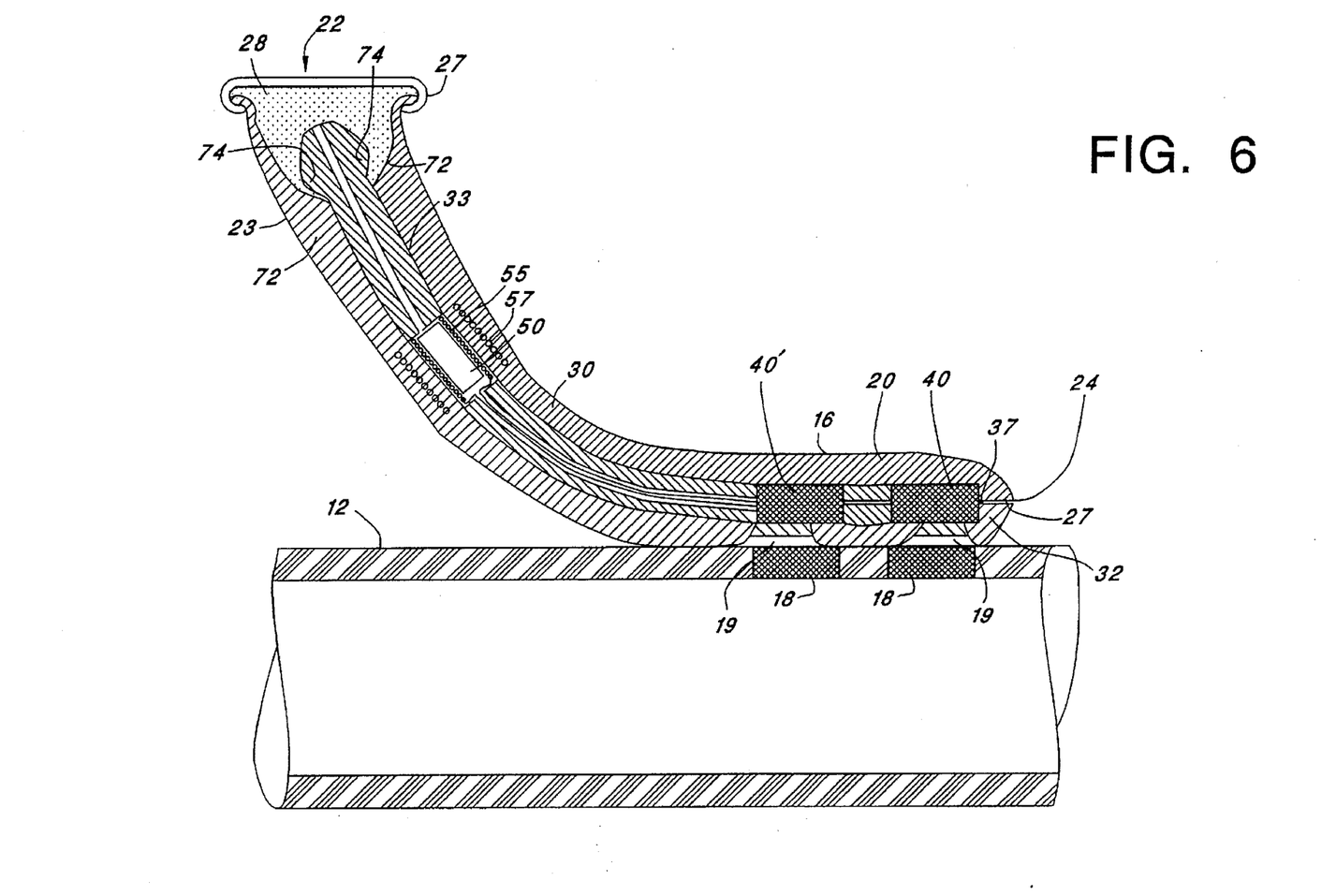
FIG. 6 is a cross sectional fragmentary view of the exterior sensor arrangement of FIG. 4, illustrating the internal structure of the introducer, implantable shunt, and replaceable catheter.

As noted above, protective mechanisms of the body generally operate on the sensors 40 and electrodes 40' to protect the body from the invasion of these foreign objects. To this end, blood clotting and tissue growth may occur proximate to where the sensors 40 or electrodes 40' are situated resulting in a reduced effectiveness and decrease in service life of the sensors 40 or electrodes 40'. To combat these undesirable effects, as well as to increase the reliability and quality of the sensors 40 or electrodes 40', the preferred introducer 20 acts as a protective sheath surrounding the sensors 40 and electrodes 40'. As seen in FIGS. 5 and 6, the preferred introducer 20 is a silicone rubber sheath placed around the sensors 40 and electrodes 40' which allows some substances to permeate through while blocking other bodily fluids. This protective sheath also prevents potentially dangerous chemicals that may be included in a given sensor 40 from getting into the body. The operative elements of sensors 40 or electrodes 40' are only exposed to the blood flow at preselected sites or windows 19.

The composition and permeability of the protective sheath is dependent on the type, location and function of the sensors 40 and electrodes 40' introduced into the patient. As discussed earlier, when the sensors or electrodes are placed in a vascular member, such as an artery or vein, for the purpose of sensing the pH of the blood, the glucose level, or oxygen level, present in the bloodstream, the sensors 40 or electrodes 40' are sealably isolated from the blood flow by a protective sheath of silicon rubber with only a minimal required exposure to the blood through a series of windows 19. The silicon rubber protective sheath allows oxygen to permeate through the silicon rubber sheath while blocking other blood components from gathering around the sensors 40 or electrodes 40' except through the designated windows 19.

Figures 7A, 7B, 7C:
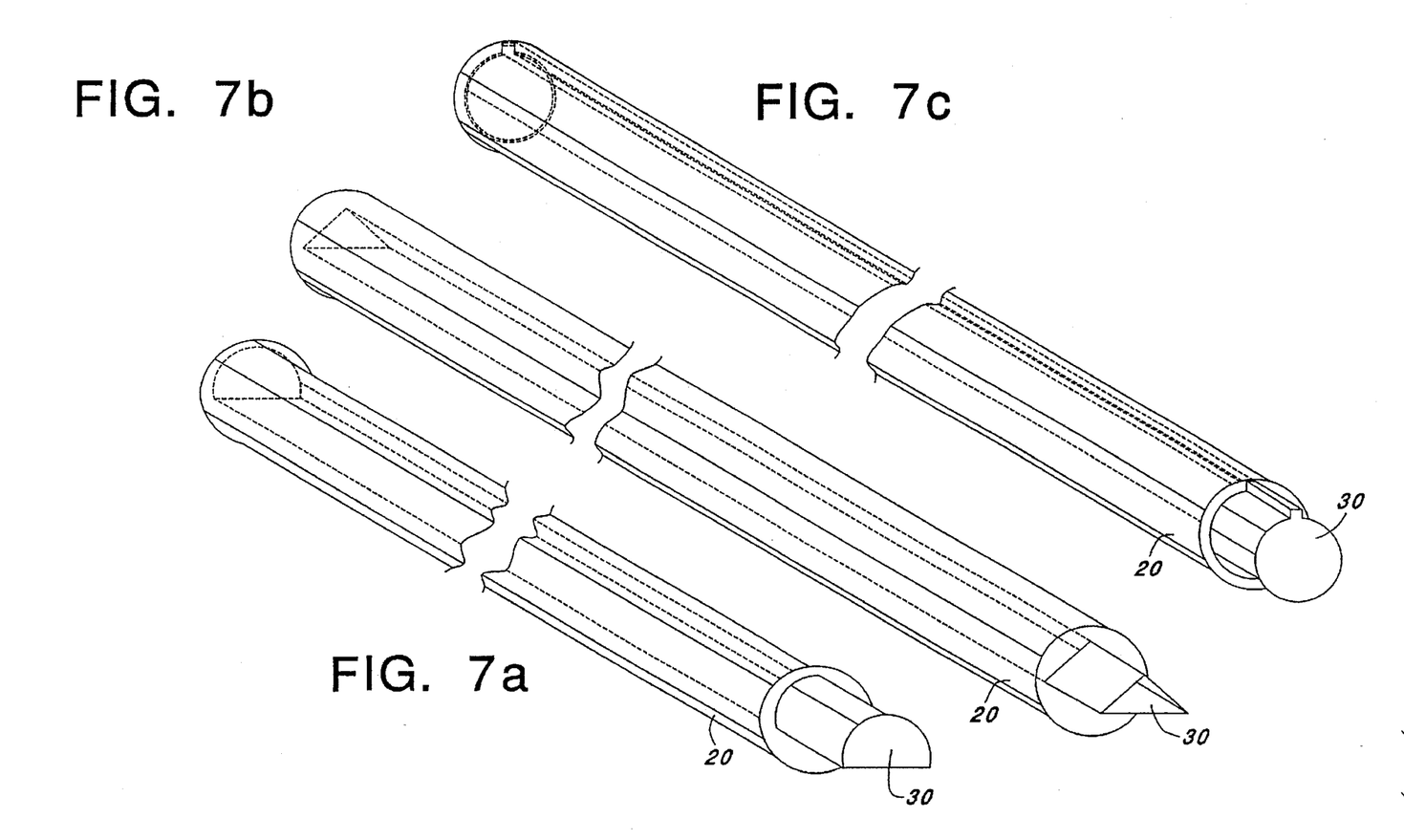
FIGS. 7a, 7b and 7c are end perspective views of the introducer and replaceable catheter illustrating specialized alignment configurations that allow the replaceable catheter to be inserted in the introducer in a single predetermined orientation.

In such an arrangement, it is important that the sensors 40 or electrodes 40' be properly aligned and oriented with respect to the windows 19. Accordingly, the replaceable catheter 30 and the interior conduit 25 of the introducer 20 may be formed in specialized mating configurations to assure that the active sensors 40 and electrodes 40' are aligned with the windows 19. Several examples of the specialized mating configurations are illustrated in FIGS. 7a, 7b and 7c. These specialized mating configurations permit the replaceable catheter 30 to be inserted in the introducer 20 in a single orientation only. The active sensors 40 or electrodes 40' are then disposed on the replaceable catheter 30 at a particular orientation and particular axial position such that it aligns with similarly situated windows 19 in in the introducer 20.

The preferred embodiment of the introducer 20 also includes a distal end vent 27 (FIGS. 5 and 6) which allows communication between the interior conduit 25 of the introducer 20 and the interior passage 14 of the implantable shunt 12. (See FIGS. 5 and 6.) As the replaceable catheter 30 is inserted in the introducer 20, any bodily fluids or chemical substances residing within the introducer 20 are forced out, thus eliminating problems caused by the accumulation and stagnation of blood or other fluids within the introducer 20. The distal end 32 of the replaceable catheter 30 preferably includes a sealing extension 37 which seals the distal end vent 27 after the introducer 20 has been evacuated of all fluids.

Another method or technique for combating the natural protective mechanisms is the introduction of specified liquid chemicals or substances into the catheter system so as to be near the sensors or electrodes. The replaceable catheter system optionally includes one or more reservoirs adapted to introduce a liquid chemical via the introducer to a site proximate the sensors or electrodes. The introduction of the liquid chemicals effectively prevents, or reduces, formation of tissue growth or blood clots near the distal end of the replaceable catheter which may interfere with the operation of the sensors or electrodes. In addition, the introduction of selected fluids can be used to prevent infection and provide medication at the site of implantation. The liquid chemicals or fluids can also be introduced for the purpose of anesthetizing surrounding neurostructure, or to introduce a calibration or control substance into the investigated site.

The preferred liquid chemicals or substances include an anti-tissue growth chemical substance, an anticoagulant or Antithrombogenic substance such as heparin, or an antibacterial substance such as commonly used antibiotics. In addition, other substances such as a simple saline solution may be contained within a reservoir for introduction directly near the sensor to adjust or calibrate the operation of the sensors.

As described above, the introducer 20 is preferably a specially designed member extending from the patient's skin to the implantable shunt 12. Moreover, the replaceable catheter 30 is typically disposed within the interior conduit of the introducer 20 and at a selected orientation which directs the replaceable catheter 30 and active sensors 40 to the appropriate implantation or investigated site. This interior conduit or main lumen may also be used to transport selected chemical substances at preselected infusion rates from the reservoirs to the implantation or investigated site for the aforementioned purposes. In yet another embodiment, the introducer may include one or more secondary fluidic lumens, each of the secondary lumens connecting one or more internal reservoirs to the distal end of the introducer to transport selected substances at preselected infusion rates to the implantation site. The distal end of the introducer is preferably proximate to the distal end of the replaceable catheter as well as the sensors and/or electrodes.

The preferred internal reservoirs are located near the proximal end of the introducer just beneath the patient's skin. If desired, the reservoirs are constructed so as to be replenished by injecting a suitable volume of the liquid substance through the patient's skin directly into the reservoirs. The actual volume of any given reservoir can be particularly suited for the application in which it is used.

Yet another method or technique for combating the natural protective mechanisms of isolating tissue growth is to apply a coating of certain beta ray emissive material to the internal or implantable components. The beta ray emissive material is preferably placed on exterior surfaces of the introducer and the exterior surfaces of the replaceable catheter. The beta ray emissive material provides a protective coating of tissue growth inhibitors that allows selected substances to permeate through to the sensors while preventing tissue growth on the replaceable catheter system.

Referring again to FIG. 5 and FIG. 6, one or more physiological or chemical sensors 40 and/or electrodes 40' are oriented such that they are directly or indirectly exposed to body fluids within the implantable shunt 12. These sensors 40 and/or electrodes 40' are preferably placed along the length of the replaceable catheter 30, or at its distal end 32, and are electrically connected to an electronics package 50. The electronics package 50 is preferably implanted and withdrawn with the implanted sensors 40 and/or electrodes 40'. The electronics package 50 includes appropriate circuitry for driving or receiving electrical signals sent to, or received from, the sensors 40 and/or electrodes 40'. For example, the circuitry within the electronics package 50 may comprise a sensor module such as the module described in U.S. Pat. No. 4,494,950, including a signal processor and telemetry system for sending or receiving a sensor signals. Alternatively, the electronics package may comprise telemetry circuitry such as that described in U.S. Pat. No. 4,944,299, also incorporated herein by reference, that permits data to be transmitted between two coils in close proximity to each other at a high data rate. The manner of coupling power and data to and from an implanted sensor or electrode or other implanted circuitry to the electronics package 50 may be conventional, e.g., as described in U.S. Pat. Nos. 3,751,605; 4,741,339; and 4,809,712.

The sensor signals originate at the sensor 40, are passed to the electronics package 50 and are then electrically coupled to a control device (not shown), via a coupler means. The coupler means serves the function of a connector, and comprises, by way of example, an internally placed coil 55 proximate the electronics package 50 inductively coupled to a second external coil 57 aligned with the internally placed coil 55 thereby providing transformer coupling so that electrical signals can readily pass therebetween. The second external coil 57 is preferably disposed apart from the implantable shunt 12 and is electrically connected to the control device.

Alternative embodiments of the invention also contemplate that other means, besides inductive coupling may be used to couple the electronics package with the control device, both for data and power transfer. For example, optical signals may be coupled between appropriate optical transmitters and receivers located on the introducer and the replaceable catheter. Ultrasound signals may also be used, as may capacitive coupling, electromagnetic radiation, or even direct electrical connections. Indeed, there is virtually no limitation on the type of coupling that may be used between the control device and the replaceable catheter in order to practice the invention. Further, it should be noted that while data is normally transferred from one or more sensors to the control device, it is also possible for data to be sent from the control module to the sensors, as required, e.g., for diagnostic, control, and/or calibration purposes.

The implanted control device may merely comprise a data collection and processing means to facilitate the command and control functions for the sensor or alternatively may control a medication release system that operates in response to the sensor signals received from the sensors, and adapted for dispensing selected medication to the patient. Specifically, the sensor signals from the sensor are processed by the control device which in turn provides controlled dispensing of selected medication into the replaceable catheter from a medication dispensing system associated with the control device. Alternatively, the sensor signal may be telemetered to an external monitoring system or signal processor, such as the module described in U.S. Pat. No. 4,494,950, the output of which may be utilized to control the operation of an external medication infusion device (not shown) which introduces controlled amounts of a medication in response to the sensor signals.

To ensure the proper coupling of electrical signals between the electronics package 50 and the control device as well as proper axial alignment of the replaceable catheter 30 and introducer 20, the replaceable catheter system 10 preferably includes an indexing means comprising a fixed shoulder or mating stop 72 in the interior conduit 25 of the introducer 20 and corresponding engagement extension or mating stop 74 on the exterior surface 33 of the replaceable catheter 30. The mating stops 72 and 74 are situated such that they mechanically or physically engage one other when the sensors 40 are properly aligned with the windows 19. These mating stops 72 and 74 are preferably located near the proximal end of the introducer 20 and replaceable catheter 30, respectively. Alternatively, the indexing means may comprise electrical, optical or magnetic stops that electrically, optically, or magnetically sense the correct position of the replaceable catheter 30 with respect to the introducer 20 and/or implantable shunt 12.

From the foregoing, it should be appreciated that the present invention thus provides a readily replaceable catheter system for physiological or chemical sensors and/or stimulating electrodes and/or fluid delivery systems which allows for the replacement of such sensors and electrodes and fluid delivery tubes without a time consuming and expensive surgical procedure. Further, it will be apparent that various changes may be made in the form, construction and arrangement of the parts thereof without departing from the spirit and scope of the invention or sacrificing all of its material advantages, the forms hereinbefore described being merely exemplary embodiments thereof. To that end, it is not intended that the scope of the invention be limited to the specific embodiments illustrated and described. Rather, the scope of the invention is to be determined by the appended claims, or their equivalents.

What is claimed is:

1. A replaceable catheter system comprising:
   a surgically implantable shunt;
   a replaceable catheter adapted to extend from a patient's skin to the implantable shunt; and
   a sensor/electrode connected to the replaceable catheter and placed in operative association with the implantable shunt;
   whereby the sensor/electrode can be readily replaced after being implanted by removing the replaceable catheter from the implantable shunt and a new sensor, electrode, or tube can be placed at the implantable shunt.

2. The replaceable catheter system of claim 1 further comprising an introducer of biocompatible material adapted for housing the replaceable catheter, the introducer having a proximal end, a distal end and a conduit between the proximal end and the distal end, the replaceable catheter being disposed within the conduit.

3. The replaceable catheter system of claim 2 wherein the distal end of the introducer further extends into and within the implantable shunt such that the sensor/electrode resides in an interior passage of the implantable shunt.

4. The replaceable catheter system of claim 2 wherein the introducer further extends in juxtaposition relation with the implantable shunt such that the sensor/electrode is placed proximate an exterior surface of the implantable shunt.

5. The replaceable catheter system of claim 2 wherein the introducer further comprises a protective sheath surrounding the sensor/electrode thereby isolating the sensor/electrode from the patient's protective mechanisms when implanted, the protective sheath being further adapted to allow selected substances to permeate the sheath while blocking other substances.

6. The replaceable catheter system of claim 5 wherein the introducer further includes:
   a distal end vent which allows communication between an interior passage of the introducer and the exterior such that any bodily fluids or chemical substances residing within the introducer are flushed out by the replaceable catheter as the replaceable catheter is inserted in the introducer; and a sealing extension disposed at a distal end of the replaceable catheter which seals the distal end vent as the replaceable catheter is fully inserted in the introducer.

7. The replaceable catheter system of claim 2 further comprising a protective coating of tissue growth inhibitors disposed on exterior surfaces of the introducer and the replaceable catheter, the protective coating being further adapted to allow selected substances to permeate through to the electronic sensing means while preventing tissue growth on or near the replaceable catheter system.

8. The replaceable catheter system of claim 2 further comprising:

a control device adapted for implantation within the patient;

an electronics package disposed proximate the replaceable catheter and operatively associated with the sensor/electrode; and a coupling means for electrically coupling power and data signals between the electronics package and the implanted control device.

9. The replaceable catheter system of claim 2 further comprising an indexing means on the introducer and replaceable catheter for axially locating the replaceable catheter at a predetermined position within the introducer.

10. The replaceable catheter system of claim 9 wherein the indexing means comprises mating internal and external stops on the introducer and replaceable catheter, respectively.

11. The replaceable catheter system of claim 2 further comprising:

one or more internally implanted reservoirs of selected fluids disposed near the proximal end of the introducer; and one or more secondary fluidic lumens disposed within the introducer and in communication with the reservoirs, the secondary fluidic lumens are adapted for directing the selected fluids from the reservoirs to predetermined locations proximate to the distal end of the replaceable catheter and introducer.

12. The replaceable catheter system of claim 11 wherein a selected fluid is an Antithrombogenic, anticoagulant, antibiotic, or anesthetizing substance.

13. The replaceable catheter system of claim 1 wherein the implantable shunt is an arteriovenous shunt.

14. The replaceable catheter system of claim 1 wherein the sensor/electrode comprises at least one physiological/chemical sensor.

15. The replaceable catheter system of claim 1 wherein the sensor/electrode comprises at least one stimulating electrode.

* * * * *